United States Patent
Wei et al.

(10) Patent No.: US 6,326,608 B1
(45) Date of Patent: Dec. 4, 2001

(54) POLARIZATION-TYPE LASER DETECTION SYSTEM

(75) Inventors: Her-Ting Wei, Taoyuan Hsien; Guang-Ming Shle, Taoyuan; Dong Chang, Taoyuan Hsien, all of (TW)

(73) Assignee: Chung-Shan Institute of Science and Technology, Taoyun (TW)

( * ) Notice: Subject to any disclaimer, the term of this patent is extended or adjusted under 35 U.S.C. 154(b) by 0 days.

(21) Appl. No.: 09/350,963

(22) Filed: Jul. 9, 1999

(51) Int. Cl.[7] .................................................. G02F 1/01
(52) U.S. Cl. ..................... 250/225; 250/221; 250/222.1
(58) Field of Search ......................... 356/73, 369, 371, 356/342, 343, 338; 250/225, 221, 222.1, 574, 573

(56) References Cited

U.S. PATENT DOCUMENTS

| | | | |
|---|---|---|---|
| 3,646,352 | * 2/1972 | Bol et al. | 250/218 |
| 3,788,742 | * 1/1974 | Garbuny | 356/5 |
| 4,459,023 | * 7/1984 | Reich et al. | 356/237 |
| 5,076,696 | * 12/1991 | Cohn et al. | 356/369 |
| 5,471,298 | * 11/1995 | Moriya | 356/336 |
| 5,815,265 | * 9/1998 | Moelter et al. | 356/338 |

* cited by examiner

*Primary Examiner*—John R. Lee
*Assistant Examiner*—Eric Spears
(74) *Attorney, Agent, or Firm*—Jiawei Huang; J. C. Patents

(57) ABSTRACT

A polarization-type laser detection system is provided, which is capable of distinguishing between a reflected light signal from a target object and a back-scattered light signal from a mass of suspended particles in the air. This allows the laser detection system to be reliably operable under bad weather conditions when the air is filled with suspended particles. The laser detection system includes a laser means for producing a linearly-polarized laser beam which is the directed to a specified direction for target detection. When echoed back, the echoed signal is first polarized by an analyzer lens into a direction that is perpendicular to the direction in which the emitted laser beam is polarized. Further, a Fresnel lens is used for focusing the emerging light from the analyzer lens into a focal point where an optical detection module is mounted. The opto-electrical signals from the two optical detectors are used to indicate whether the echoed light signal is a back-scattered light signal or a reflected light signal from a target object. This laser detection system is therefore suitable for use under all weather conditions.

15 Claims, 3 Drawing Sheets

POLARIZATION-TYPE LASER DETECTION SYSTEM

BACKGROUND OF THE INVENTION

1. Field of the Invention

This invention relates to laser technology, and more particularly, to a polarization-type laser detection system which is capable of distinguishing between a reflected light signal from a target object and a back-scattered light signal from a mass of suspended particles in the air.

2. Description of Related Art

FIG. 1 is a schematic diagram of a conventional laser detection system. As shown, this laser detection system includes a control unit 10, a laser emitter 20, and an optical receiver 30. This laser detection system is used to detect whether any target object is present nearby. In the case of a target object 40 is present nearby, the laser beam from the laser emitter 20 will be reflected back by the target object 40 and received by the optical receiver 30. The received light is then analyzed by the control unit 10 to indicate the presence of the target object 40.

One drawback to the foregoing laser detection system, however, is that, under bad weather conditions when the air is filled with suspended particles, the emitted laser beam from the laser emitter 20 would be scattered back, causing the optical receiver 30 to received a back-scattered light signal that would make the control unit 10 unable to perform the intended target detection. The laser detection system would therefore operate improperly under bad weather conditions.

SUMMARY OF THE INVENTION

It is therefore an objective of this invention to provide a laser detection system, which is capable of distinguishing between a reflected light signal from a target object and a back-scattered light signal from suspended particles in the air, so as to allow the laser detection system to be nevertheless reliably operable under bad weather conditions.

In accordance with the foregoing and other objectives of this invention, a new laser detection system, called polarization-type laser detection system, is provided.

The polarization-type laser detection system of the invention includes the following system components: laser means for generating a linearly-polarized laser beam which is polarized in a first direction; an emitting optical system, coupled to the laser means, for directing the laser beam to a specified direction for target detection; a reception optical system for receiving the echoed light signal from the emitted laser beam, if any; the reception optical system including: an analyzer lens (AL) for blocking a first direction of the echoed light signal and passing a second direction that is perpendicular to the first direction in which the emitted laser beam is polarized; and a Fresnel lens for focusing the emerging light from the AL into a focal point; an optical detection module, including a first optical detector disposed at the focal point of the Fresnel lens; and a second optical detector disposed beside the first optical detector.

The polarization-type laser detection system of the invention further comprises a laser drive circuit, coupled to the laser means, for driving the laser means to produce the linearly-polarized laser beam. The emitting optical system includes a stop, optically coupled to the laser means, for restricting the amount of the laser beam emitted from the laser means; and a collimator, optically coupled to the stop, for collimating the emerging light from the stop, with the collimated light then being outputted from the emitting optical system for target detection. Further, the polarization-type laser detection system of the invention comprises a pre-amplification circuit, coupled to the first and second optical detectors, for amplifying the first and second opto-electrical signals generated by the first and second optical detectors.

The foregoing laser detection system is capable of distinguishing whether the echoed light is a back-scattered light signal from suspended particles in the air or a reflected light signal from a solid target object. This allows the laser detection system to be nevertheless utilizable under bad weather conditions when suspended particles in the air could result in false detection.

BRIEF DESCRIPTION OF DRAWINGS

The invention can be more fully understood by reading the following detailed description of the preferred embodiments, with reference made to the accompanying drawings, wherein.

DETAILED DESCRIPTION OF PREFERRED EMBODIMENTS

The principles utilized by the invention are first depicted in the following with reference to FIG. 2 and FIG. 3.

Figure 1:
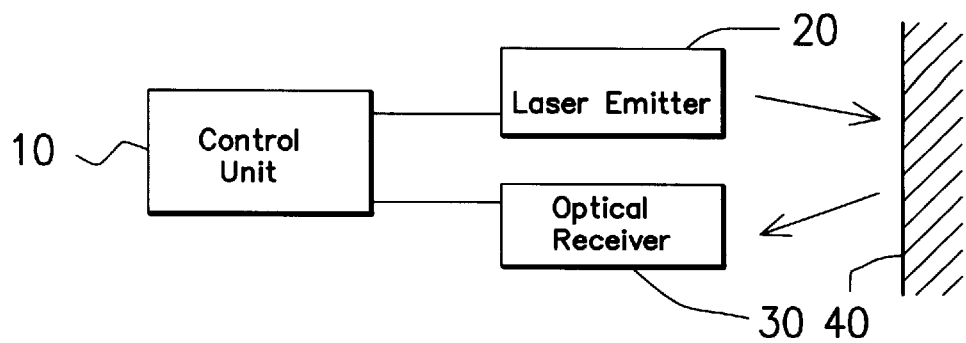
FIG. 1 (PRIOR ART) is a schematic diagram showing a conventional laser detection system.
Figure 2:
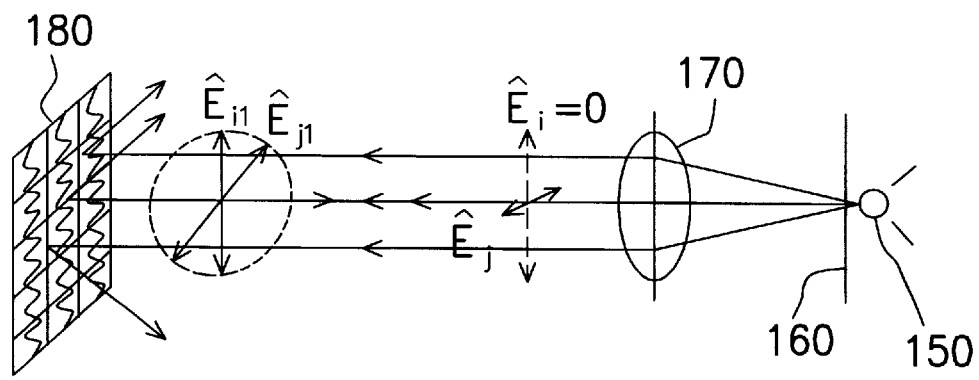
FIG. 2 is a schematic diagram used to depict the reflective effect of a linearly polarized laser beam striking on a solid target object.

FIG. 2 is a schematic diagram used to depict the reflective effect of a linearly polarized laser beam striking on a solid target object. As shown, a linear-polarization laser diode 150 is used to generate a linearly-polarized laser beam, which then passes a stop 160 and a collimator 170. The collimated laser beam is polarized only in the horizontal direction (in FIG. 2, i denotes the vertical direction while j denotes the horizontal direction); and therefore there is no vertically-polarized component in the collimated laser beam (i.e., $\hat{E}_i=0$ and $\hat{E}_j \neq 0$). When this linearly-polarized laser beam strikes a solid target object 180, it would be reflected back, with the reflected light signal containing polarized components both in the vertical direction and the horizontal direction, and which are substantially equal in intensity, i.e., the reflected light signal contains a vertically-polarized component $\hat{E}_{j1}$ and a horizontally-polarized component $\hat{E}_{j1}$, and $\hat{E}_{j1}=\hat{E}_{j1}$.

Figure 3:
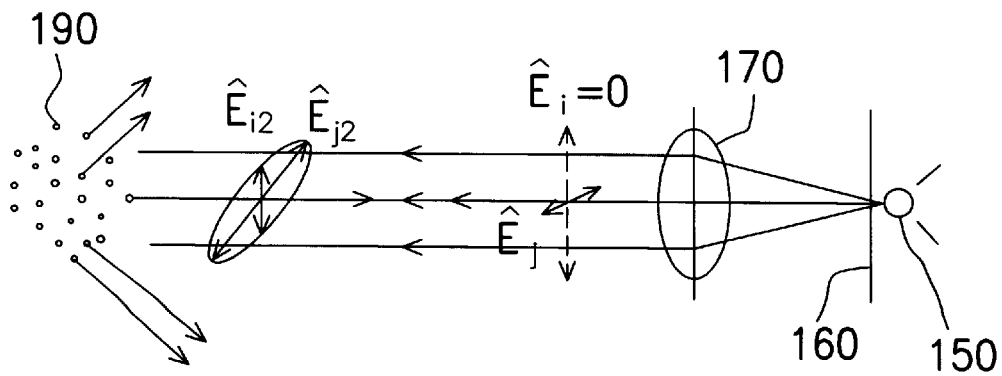
FIG. 3 is a schematic diagram used to depict the scattering effect of a linearly polarized laser beam striking on a mass of suspended particles in the air.

FIG. 3 is a schematic diagram used to depict the scattering effect of a linearly-polarized laser beam striking on a mass of suspended particles in the air. As shown, a linear-polarization laser diode 150 is used to generate a linearly-polarized laser beam, which then passes a stop 160 and a collimator 170. The collimated laser beam is polarized only in the horizontal direction, i.e., $\hat{E}_i=0$ and $\hat{E}_j\neq 0$. When this linearly polarized laser beam meets a mass of suspended particles in the air, it would be scattered to all directions, with the vertically-polarized components $\hat{E}_{i2}$ significantly smaller in intensity than the horizontally-polarized components $\hat{E}_{j2}$.

It can be learned from the foregoing description that the case of FIG. 2 and the case of FIG. 3 would provide two different forms of echoed light signals, respectively from a solid target object and a mass of suspended particles in the air. These two different characteristics are then utilized by the invention to distinguish whether the echoed light signal is resulted either from a solid target object or a mass of suspended particles in the air.

Figure 4:
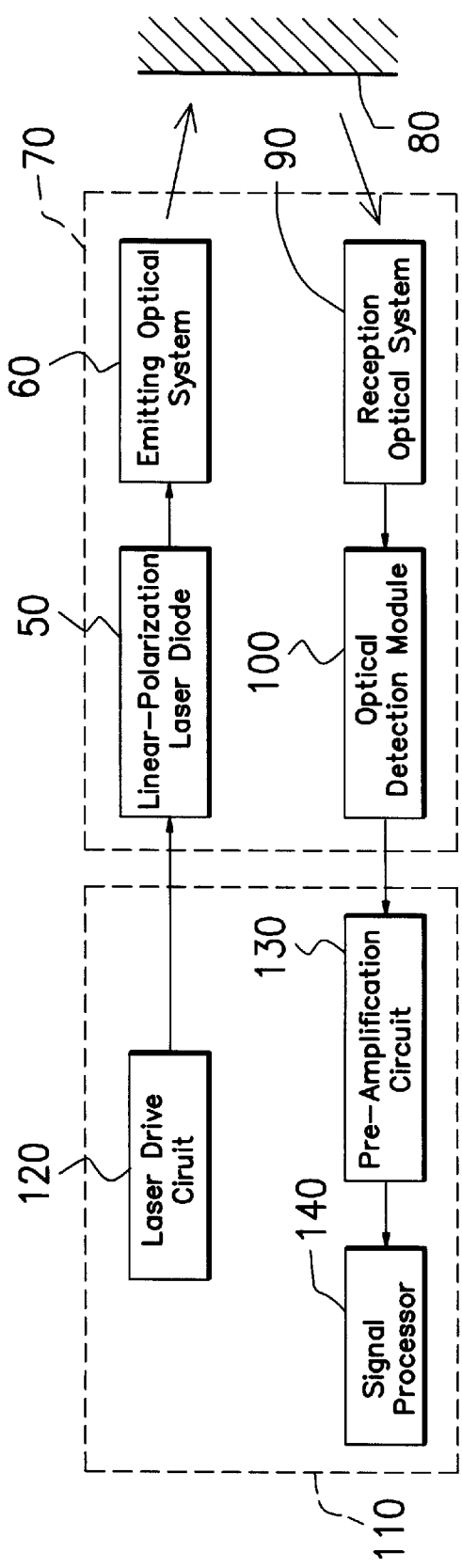
FIG. 4 is a schematic block diagram of the polarization-type laser detection system according to the invention.

FIG. 4 is a schematic block diagram of the polarization-type laser detection system according to the invention. As shown, the polarization-type laser detection system of the invention includes a laser emitter/receiver unit 70 and a control unit 110. The laser emitter/receiver unit 70 further includes a linear-polarization laser diode 50, an emitting optical system 60, a reception optical system 90, and an optical detection module 100. The control unit 110 includes a laser drive circuit 120, a pre-amplification circuit 130, and a signal processor 140.

The laser drive circuit 120 is used to drive the laser diode 50 to produce a linearly-polarized laser beam. The pre-amplification circuit 130 is used to amplify the output opto-electrical signal from the optical detection module 100. The signal processor 140 is used to process the amplified output from the pre-amplification circuit 130 to determine the detection result.

Figure 5:
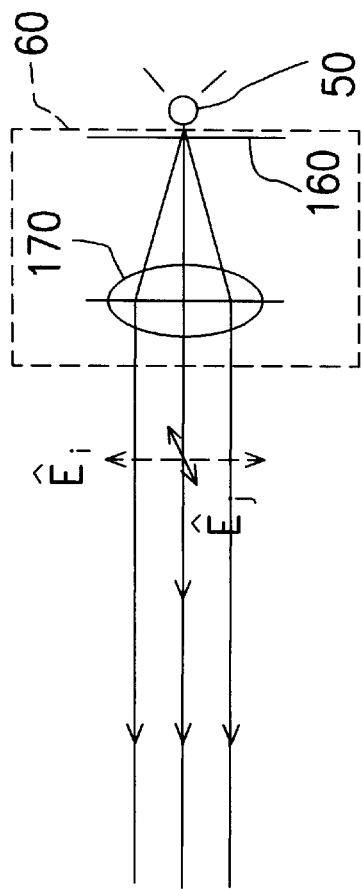
FIG. 5 is a schematic diagram showing more detailed structure of the emitting optical system utilized by the invention.

FIG. 5 shows more detailed structure of the emitting optical system 60 which is optically coupled to the laser diode 50. As shown, the emitting optical system 60 includes a stop 160 and a collimator 170. The laser diode 50 is disposed at the focal point of the collimator 170, so that the laser beam from the laser diode 50 can be collimated by the collimator 170 into parallel rays. The stop 160 is disposed between the laser diode 50 and the collimator 170, and is used to limit the amount of the emitted laser beam. The collimated laser beam is polarized only in the horizontal direction (in FIG. 5, i denotes the vertical direction while j denotes the horizontal direction); and therefore there is no vertically-polarized component in the collimated laser beam (i.e., $\hat{E}_i=0$ and $\hat{E}_j\neq 0$.

Figure 6:
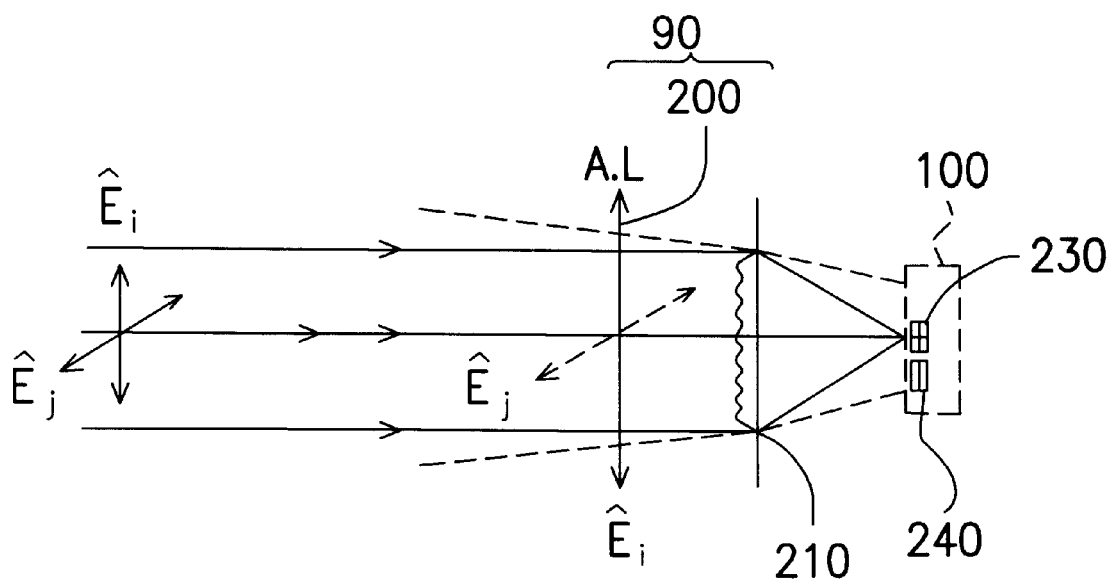
FIG. 6 is a schematic diagram showing more detailed structure of the reception optical system and the optical detection module utilized by the invention.
Figure 7:
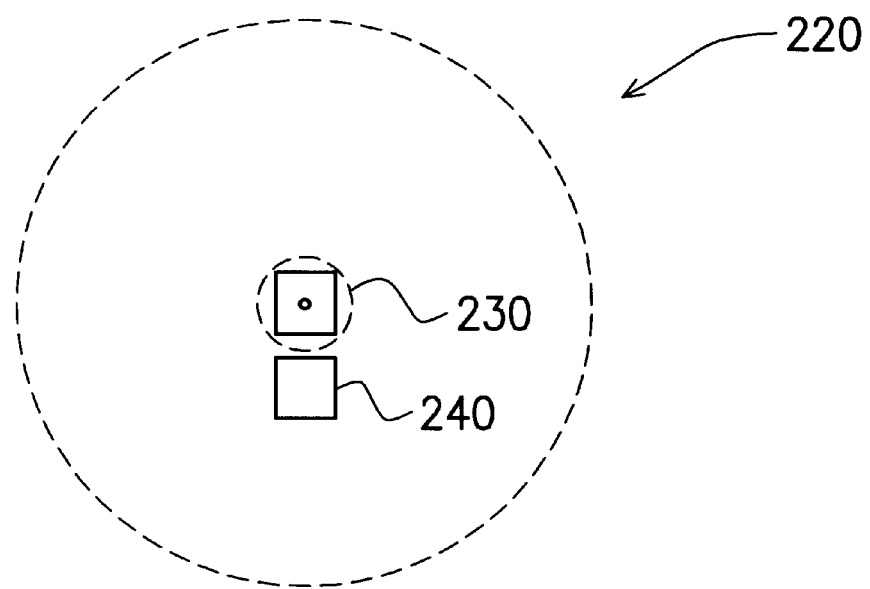
FIG. 7 is a schematic diagram showing the spatial arrangement of a pair of optical detectors in the optical detection module utilized by the invention.

FIG. 6 shows more detailed structure of the reception optical system 90 and the optical detection module 100 shown in FIG. 4. As shown, the reception optical system 90 includes an analyzer lens (AL) 200 and a Fresnel lens 210; and the optical detection module 100 includes a pair of optical detectors: a first optical detector 230 and a second optical detector 240. As illustrated in FIG. 7, the optical detection module 100 is disposed on the focal plane of the Fresnel lens 210 in such a manner that the first optical detector 230 is positioned at the focal point of the Fresnel lens 210, while the second optical detector 240 is positioned beside the first optical detector 230 and beyond the focal point of the Fresnel lens 210.

The Fresnel lens 210 is disposed between the AL 200 and the optical detection module 100. In accordance with the invention, the AL 200 is oriented in such a manner as to allow only the vertically-polarized component of the incident light to pass therethrough, while rejecting all horizontally-polarized component. The emerging light from the AL 200 is then focused by the Fresnel lens 210 onto the optical detection module 100.

Referring back to FIG. 4, in the case that the output laser beam from the emitting optical system 60 strikes on a solid target object 80, it would be reflected back, with the reflected light signal containing a vertically-polarized component $\hat{E}_i$ and a horizontally polarized component $\hat{E}_j$, and these two components are substantially equal in intensity, i.e., $\hat{E}_i=\hat{E}_j$. When the reflected light signal is received by the reception optical system 90, it first meets the AL 200 which allows only the vertically-polarized component $\hat{E}_i$ to pass therethrough, while rejecting the horizontally-polarized component $\hat{E}_j$. The emerging light from the AL 200 is then focused by the Fresnel lens 210 onto the first optical detector 230 which is disposed at the focal point of the Fresnel lens 210, causing the first optical detector 230 to be activated to generate an opto-electrical signal. In this case, however, the second optical detector 240 generates no opto-electrical signal. Therefore, the condition of the first optical detector 230 being activated and the second optical detector 240 being deactivated can be used to indicate that the echoed light signal is a reflected light signal resulted from a solid target object.

On the other hand, in the case that the output laser beam meets a mass of suspended particles in the air, the laser beam would be scattered to all directions, with the back-scattered light signal containing both a horizontally-polarized component and a vertically-polarized component. The AL allows only the vertically-polarized component $\hat{E}_i$ to pass therethrough, and it would not be focused by the Fresnel lens 210 solely at the focal point where the first optical detector 230 is disposed; and therefore, the second optical detector 240 can also detect the back-scattered light signal. The opto-electrical signal generated by the second optical detector 240 is then amplified by the pre-amplification circuit 130 and then transferred to the signal processor 140. The signal processor 140 operates in such a manner that when an opto-electrical signal is received from the second optical detector 240, it indicates that the echoed light signal is a back-scattered light signal resulted from a mass of suspended particles in the air and not from a solid target object.

In conclusion, the invention provides a polarization-type laser detection system capable of distinguishing whether the echoed light signal is a reflected light signal resulted from a solid target object or a back-scattered light signal resulted from a mass of suspended particles in the air. This allows the laser detection system to be nevertheless reliably operable under bad weather conditions when suspended particles in the air could result in false detection.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A polarization-type laser detection system, which comprises:

(a) laser means for generating a linearly-polarized laser beam which is polarized in a first direction;

(b) an emitting optical system, coupled to the laser means, for directing the laser beam to a specified direction for target detection;

(c) a reception optical system for receiving any echoed light signal of the emitted laser beam due to the emitted laser beam striking on a solid target object or a mass of suspended particles in the air; the reception optical system including:

an analyzer lens for blocking a first direction of the echoed light signal and passing a second direction that is perpendicular to the first direction in which the emitted laser beam is polarized; and a Fresnel lens for focusing the emerging light from the analyzer lens into a focal point;
(d) an optical detection module, including
a first optical detector disposed at the focal point of the Fresnel lens; and
a second optical detector disposed beside the first optical detector.

2. The polarization-type laser detection system of claim 1, wherein the laser means is a linear-polarization laser diode.

3. The polarization-type laser detection system of claim 1, further comprising:
a laser drive circuit, coupled to the laser means, for driving the laser means to produce the linearly-polarized laser beam.

4. The polarization-type laser detection system of claim 1, wherein the emitting optical system includes:
a stop, optically coupled to the laser means, for restricting the amount of the laser beam emitted from the laser means.

5. The polarization-type laser detection system of claim 4, wherein the emitting optical system further includes:
a collimator, optically coupled to the stop, for collimating the emerging light from the stop, with the collimated light then being outputted from the emitting optical system for target detection.

6. The polarization-type laser detection system of claim 1, further comprising:
a pre-amplification circuit, coupled to the optical detection module, for amplifying the opto-electrical signals generated by the first optical detector and the second optical detector.

7. The polarization-type laser detection system of claim 6, further comprising:
a signal processor, coupled to the pre-amplification circuit, for processing the amplified opto-electrical signals from the optical detection module to indicate whether the echoed light signal is a back-scattered light signal or a reflected light signal from a target object.

8. A polarization-type laser detection system, which comprises:
(a) laser means for generating a linearly-polarized laser beam which is polarized in a first direction;
(b) a laser drive circuit, coupled to the laser means, for driving the laser means to produce the linearly-polarized laser beam;
(c) an emitting optical system, coupled to the laser means, for directing the laser beam to a specified direction for target detection;
(d) a reception optical system for receiving the echoed light signal from the emitted laser beam, if any; the reception optical system including:
an analyzer lens for blocking a first direction of the echoed light signal and passing a second direction that is perpendicular to the first direction in which the emitted laser beam is polarized; and
a Fresnel lens for focusing the emerging light from the analyzer lens into a focal point;
(e) an optical detection module, including
a first optical detector disposed at the focal point of the Fresnel lens; and
a second optical detector disposed beside the first optical detector;
(f) a pre-amplification circuit, coupled to the optical detection module, for amplifying the opto-electrical signals generated by the first optical detector and the second optical detector; and (g) a signal processor, coupled to the pre-amplification circuit, for processing the amplified opto-electrical signals from the optical detection module to indicate whether the echoed light signal is a back-scattered light signal or a reflected light signal from a target object.

9. The polarization-type laser detection system of claim 8, wherein the laser means is a linear-polarization laser diode.

10. The polarization-type laser detection system of claim 8, wherein the emitting optical system including:
stop, optically coupled to the laser means, for restricting the amount of the laser beam emitted from the laser means; and
a collimator, optically coupled to the stop, for collimating the emerging light from the stop, with the collimated light then being outputted from the emitting optical system for target detection.

11. A polarization-type laser detection system, which comprises:
laser means for generating a linearly-polarized laser beam which is polarized in a first direction and which is directed to a specified direction for target detection;
an analyzer lens for blocking a first direction of an echoed light signal of the echoed light signal and passing a second direction that is perpendicular to the first direction in which the emitted laser beam is polarized;
a Fresnel lens for focusing the emerging light from the analyzer lens into a focal point;
a first optical detector disposed at the focal point of the Fresnel lens, capable of generating a first opto-electrical signal when light strikes thereon;
a second optical detector disposed beside the first optical detector, capable of generating a second opto-electrical signal when light strikes thereon; and
signal processor means, in response to the first and second opto-electrical signals, for indicating whether the echoed light signal is a reflected light signal resulted from a solid target object or a back-scattered light signal resulted from a mass of suspended particles in the air.

12. The polarization-type laser detection system of claim 11, wherein the laser means is a linear-polarization laser diode.

13. The polarization-type laser detection system of claim 11, further comprising:
a laser drive circuit, coupled to the laser means, for driving the laser means to produce the linearly-polarized laser beam.

14. The polarization-type laser detection system of claim 11, further comprising:
an emitting optical system including:
a stop, optically coupled to the laser means, for restricting the amount of the laser beam emitted from the laser means; and
a collimator, optically coupled to the stop, for collimating the emerging light from the stop, with the collimated light then being outputted from the emitting optical system for target detection.

15. The polarization-type laser detection system of claim 11, further comprising:
a pre-amplification circuit, coupled to the first and second optical detectors, for amplifying the first and second opto-electrical signals generated by the first and second optical detectors.

* * * * *